United States Patent [19]
Broadus et al.

[11] Patent Number: 5,605,815
[45] Date of Patent: Feb. 25, 1997

[54] NUCLEIC ACIDS ENCODING AND EXPRESSION OF PARATHYROID HORMONE-LIKE PEPTIDE

[75] Inventors: Arthur E. Broadus, New Haven; Andrew F. Stewart, North Haven; Marguerite Mangin, Old Lyme, all of Conn.

[73] Assignee: Yale University, New Haven, Conn.

[21] Appl. No.: 263,242

[22] Filed: Jun. 21, 1994

Related U.S. Application Data

[63] Continuation of Ser. No. 839,722, Feb. 18, 1992, abandoned, which is a continuation of Ser. No. 167,593, Mar. 14, 1988, abandoned.

[51] Int. Cl.$^6$ .............................. C07H 21/02; C12P 21/00
[52] U.S. Cl. .................. 435/694; 435/172.3; 435/252.3; 435/320.1; 435/252.31; 435/252.33; 435/252.34; 435/254.2; 435/254.21; 435/325; 435/360; 435/365.1; 435/367; 536/23.5
[58] Field of Search .................................. 435/69.1, 69.4, 435/172.3, 320.1, 240.2, 252.3, 252.33, 252.34, 252.31; 935/9, 27; 536/23.5, 57; 530/399

[56] References Cited

U.S. PATENT DOCUMENTS

| | | | |
|---|---|---|---|
| 4,530,901 | 7/1985 | Weissman et al. | 435/172.3 |
| 5,116,952 | 5/1992 | Martin et al. | 530/399 |

OTHER PUBLICATIONS

Mangin et al *Proc Natl Acad Sci* vol. 85 pp. 597–601 Jan. 1988 "Identification of a cDNA Encoding a Parathyroid Hormone–Like Peptide from a Human Tumor Associated with Humoral Hypercalcemia of Maglinancy".

Moseley et al *Proc. Natl Acad Sci* vol. 84 pp. 5048–5052 Jul. 1987 "Parathyroid Hormone–Related Protein Purified from a Human Lung Cancer Cell Line".

Suggs *Proc Natl Acad Sci* vol. 78 No. 11 pp. 6613–6617 Nov. 1981 "Use of Synthetic Oligonucleotides as Hybridization Probes: Isolation of Cloned cDNA Sequences for Human $\beta_2$–Microglobulin".

Stewart et al *Biochem Biophys Res Comm* vol. 46 No. 2 Jul. 31, 1987 "N–Terminal Amino Acid Sequence of Two Novel Tumor–Derived Adenylate Cyclase–Stimulating Proteins . . .".

J.D. Schermer et al., J. Bone and Mineral Research, 6(2):149–155, 1991.

T. Yasuda et al., Molecular Endocrinology 3(3):518–525, 1989.

M. Mangin et al., Gene 95:195–202, 1990.

*Primary Examiner*—Stephen G. Walsh
*Assistant Examiner*—Lorraine M. Spector
*Attorney, Agent, or Firm*—Seed and Berry LLP

[57] ABSTRACT

There is disclosed the nucleic acid and amino acid sequences for the human PTH-Like Peptide and derivatives. PTH-Like Peptide is the humoral mediator of humoral hypercalcemia of malignany or HHM which is common in patients with squamous carcinomas or renal, bladder or ovarian carcinomas with little or no evidence of skeletal disease.

22 Claims, 6 Drawing Sheets

```
-1046                                                              CCGTTTTTGTTCTTC
-1031 TAAGCAAAAGATCTCCCTCTCTAGCCGATGCTCCCCACTCAGTTCATCCCGGGAATGGGCCAGGGAGGA
-960  AGGTTCTCATGCATCGCCCCGAGCTGCCAGGCGAGCTTCGGGCTCCTTAAATTCACAGGCCAACAGCCCGC
-889  GTCCTCTCCGCGCAGGCTCCCGGTTGCCCGCGGTCCCCGGCCCAGCTCCTTGGCCTCCTCCTCGTCGGTCC
-818  GCCCCTGGTGGTCTTGGCGCCCGCTCGTCCAGCTCGGCGCGCCGGGGACGCGCCGGCTGCCCGGGGCAGTCC
-747  GCACGCCCTCGGGGATCTCGGCTCCCGGATCCGCCGCGCCGGCAGGAGCCGGCCGGGCCTGGAGGGAGCAA
-676  GCGGATGCGCCCACGCCCCCGGCACGGGGATGGCGCGACAGGGCCCGGGCTCCGGGGTGGGGCTCGGCAGA
-605  GCTCCTGACAGCTCCGGGGCTCGGCAGCGCGGGAGGGGGAGCTCCGCCGCTCGCCGCTCATTCCCGGCTC
-534  GGGGCTCCCCTCCACTCGCTCGGGCGGCGCGGGGCCCGTTCGGGCCGCCCGTCGCCGCCCCGCCCCCCGC
-463  GCGCCCGCCCGCCAGCCCGCCTGCGCCCTCGCTCGCCCCGCGCGCGTTCCTAGGGCGCCACCTCTTTGCGA
-392  CTAGCTCACTTCTCCGGCAGGTTTGCCTCGGAGCGTGTGAACATTCCTCCGCTCGGTTTTCAACTCGCCTC
-321  CAACCTGCGCCGCCCGGCCAGCATGTCTCCCCGCCCGTGAAGCGGGCTGCCGCCTCCCTGCCGCTCCGGCT
-250  GCCACTAACGACCCGCCCTCGCCGCCACCTGGCCCTCCTGATCGACGACACACGCACTTGAAACTTGTTCT
-179  CAGGGTGTGTGGAATCAACTTTCCGGAAGCAACCAGCCCACCAGAGGAGGTCCCGAGCGCGAGCGGAGACG

-108  ATG CAG CGG AGA CTG GTT CAG CAG TGG AGC GTC GCG GTG TTC CTG CTG AGC TAC
 -36  Met Gln Arg Arg Leu Val Gln Gln Trp Ser Val Ala Val Phe Leu Leu Ser Tyr

-54  GCG GTG CCC TCC TGC GGG CGC TCG GTG GAG GGT CTC AGC CGC CGC CTC AAA AGA
 -18  Ala Val Pro Ser Cys Gly Arg Ser Val Glu Gly Leu Ser Arg Arg Leu Lys Arg

1  GCT GTG TCT GAA CAT CAG CTC CTC CAT GAC AAG GGG AAG TCC ATC CAA GAT TTA
   1  Ala Val Ser Glu His Gln Leu Leu His Asp Lys Gly Lys Ser Ile Gln Asp Leu

55  CGG CGA CGA TTC TTC CTT CAC CAT CTG ATC GCA GAA ATC CAC ACA GCT GAA ATC
  19  Arg Arg Arg Phe Phe Leu His His Leu Ile Ala Glu Ile His Thr Ala Glu Ile

109  AGA GCT ACC TCG GAG GTG TCC CCT AAC TCC AAG CCC TCT CCC AAC ACA AAG AAC
  37  Arg Ala Thr Ser Glu Val Ser Pro Asn Ser Lys Pro Ser Pro Asn Thr Lys Asn

163  CAC CCC GTC CGA TTT GGG TCT GAT GAT GAG GGC AGA TAC CTA ACT CAG GAA ACT
  55  His Pro Val Arg Phe Gly Ser Asp Asp Glu Gly Arg Tyr Leu Thr Gln Glu Thr

217  AAC AAG GTG GAG ACG TAC AAA GAG CAG CCG CTC AAG ACA CCT GGG AAG AAA AAG
  73  Asn Lys Val Glu Thr Tyr Lys Glu Gln Pro Leu Lys Thr Pro Gly Lys Lys Lys

271  AAA GGC AAG CCC GGG AAA CGC AAG GAG CAG GAA AAG AAA AAA CGG CGA ACT CGC
  91  Lys Gly Lys Pro Gly Lys Arg Lys Glu Gln Glu Lys Lys Lys Arg Arg Thr Arg

325  TCT GCC TGG TTA GAC TCT GGA GTG ACT GGG AGT GGG CTA GAA GGG GAC CAC CTG
 109  Ser Ala Trp Leu Asp Ser Gly Val Thr Gly Ser Gly Leu Glu Gly Asp His Leu

379  TCT GAC ACC TCC ACA ACG TCG CTG GAG CTC GAT TCA CGG AGG CAT TGAAATTTTCA
 127  Ser Asp Thr Ser Thr Thr Ser Leu Glu Leu Asp Ser Arg Arg His End

435  GCAGAGACCTTCCAAGGACATATTGCAGGATTCTGTAATAGTGAACATATGGAAAGTATTAGAAATATTTA
 506  TTGTCTGTAAATACTGTAAATGCATTGGAATAAAACTGTCTCCCCCATTGCTCTATGAAACTGCACATTGG
 577  TCATTGTGAATATTTTTTTTTTTGCCAAGGCTAATCCAATTATTATTATCACATTTACCATAATTTATTTT
 648  GTCCATTGATGTATTTATTTTGTAAATGTATCTTGGTGCTGCTGAATTTCTATATTTTTTGTAACATAATG
 719  CACTTTAGATATACATATCAAGTATGTTGATAAATGACACAATGAAGTGTCTCTATTTTGTGGTTGATTTT
 790  AATGAATGCCTAAATATAATTATCCAAATTGATTTTCCTTTGTGCATGTAAAAATAACAGTATTTTAAATT
 861  TGTAAAGAATGTCTAATAAAATATAATCTAATTAC(A)₆₀
```

*Fig. 1*

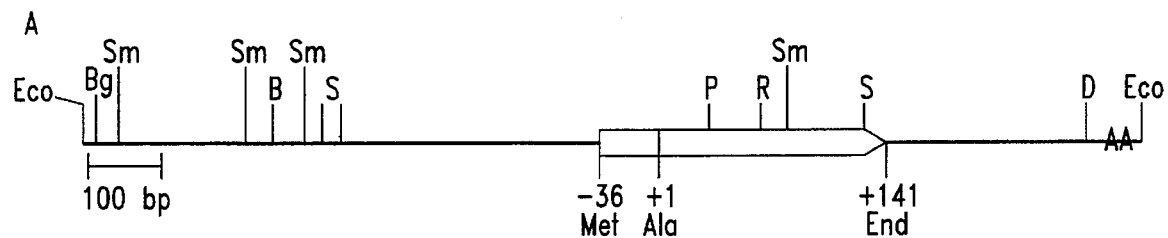

*Fig. 2*

```
              -1 +1                                              10
              Lys Arg Ser Val Ser Glu Ile Gln Leu Met His Asn Leu Gly Lys
PTH:          AAG AGA TCT GTG AGT GAA ATA CAG CTT ATG CAT ACC CTG GGA AAA
              **  *** **  *** *   ***  *** ** *   *** *   *  ** **
Peptide:      AAA AGA GCT GTG TCT GAA CAT CAG CTC CTC CAT GAC AAG GGG AAG
              Lys Arg Ala Val Ser Glu His Gln Leu Leu His Asp Lys Gly Lys
```

*Fig. 3*

```
                          6              10                15
Peptide:                Gln Leu Leu His Asp Trp Gly Lys Ser Ile Gln Asp Leu
                                            (Lys)
                                                                  A
Deduced mRNA:    5' CAPu-PyTN-PyTN-CAPy-GAPy-TGG-GGN-AAPu-PuCN -ATC-CAPu-CAC-PyTN  3'
                                                       G              T Oligonucleotide
  probe:        3' GTC -GAI- GAI -GTA- CTG -ACC-CCI-TTT- AGI- TAG-GTC -CTG-GA    5' cDNA:           5' CAG -CTC- CTC -CAT -GAC -AAG-GGG-AAG- TCC- ATC-CAA  GAT-TTA
```

*Fig. 4*

```
417  TACA GCA CTT CTG TGG GGT TTG AAA AAA AAA AAA GGA AAA CAA CAG AAG AAC ACA
140  Thr  Ala Leu Leu Trp Gly Leu Lys Lys Lys Lys Gly Lys Gln Gln Lys Asn Thr

472  TCA TAT GCA ACT AAT GAT CTC ATT ATT TAAGAGTCCCCTGTTACTTCTTTAGTCATTTCCTT
158  Ser Tyr Ala Thr Asn Asp Leu Ile Ile End

534  TGACTCTGCTACAGATAGGATTATAGGATGATGCTCCAAAGGGGACCTTGAACCTATTCACCATTATTTGT
605  CTCTTTAAGCTGGCAAACCCATCATTAAATAGCACATAAAATAGCAATCATATGGGATAAGTAGTACAGCT
676  TCAGTAATCAATGGGCAGTGGCACTAGAAAAATCTTGAGCACAGTGAATGACCTATCCTGCAAACATCTAA
747  TGGATCTCTAAAGGGTAACAAACCCTATAAATTCTGGCTTACTGCACATATTTAGTGTGTTTTAAGATAGG
818  ATCCTAACTGTATATATTTATAACTAATGTAAGGACCCTACTTTATTGCCAAAACCTATTTTTATCCATTG
889  TCTCATATATATAAACTATGTCATATATATAAACATATATATATAAACATATATGTATATAGTAAACATTC
960  AATAAATTGCAACATATT(A)100
```

Fig. 8

NUCLEIC ACIDS ENCODING AND EXPRESSION OF PARATHYROID HORMONE-LIKE PEPTIDE

CROSS-REFERENCE TO RELATED APPLICATION

This application is a file wrapper continuation of U.S. patent application Ser. No. 07/839,722, filed Feb. 18, 1992, for "CHARACTERIZATION AND EXPRESSION OF PARATHYROID HORMONE-LIKE PEPTIDE," now abandoned, which application is a file wrapper continuation of U.S. patent application Ser. No. 07/167,593, filed Mar. 14, 1988, now abandoned.

TECHNICAL FIELD

The present invention relates to Parathyroid Hormone (PTH)-Like Peptides in general, and more specifically, to the characterization, sequencing and expression of proteins having adenylate cyclase-stimulating biological activity and associated with hypercalcemia.

BACKGROUND OF THE INVENTION

The humoral hypercalcemia of malignancy factor (HHMF) is a peptide which is secreted by certain malignant tumors and renders the affected patient hypercalcemic, an often lethal biochemical complication. Malignancy-associated hypercalcemia (MAHC) has been recognized as a common clinical problem ever since the first report of the case of a 69-year-old man with malignancy and hypercalcemia (H. Zondek et al., "Die Bedeutung der Calciumbestimmung im Blute fur die Diagnose der Niereninsuffizietz," *Z. Klin. Med.* 99:128–29, 1923). Albright ("Case Records of the Massachusetts General Hospital (Case 27461)," *N. Engl. J. Med.* 225:789–91, 1941) described a patient with a renal carcinoma and a single skeletal metastasis. Because of the concomitant hypercalcemia and hypophosphatemia, Albright suggested that the tumor was secreting a systemic bone-resorbing factor that resembled parathyroid hormone in its actions. Subsequent studies confirmed that some tumor-induced hypercalcemia could be reversed by resection of isolatal malignant tumors (Plimpton et al., "Hypercalcemia in Malignant Disease Without Evidence of Bone Destruction," *Am J. Med.* 21:750–59, 1956; and Connors et al., "The Etiology of Hypercalcemia Associated with Lung Carcinoma," *J. Clin. Invest.* 35:697–98, 1956). This enabled clinicians to identify the syndrome called "humoral hypercalcemia of malignancy" or "HHM." Patients with HHM develop hypercalcemia through elaboration of systemically acting, bone-resorbing factor or factors in tumor tissue remote from bone. These patients characteristically have squamous carcinomas or renal, bladder or ovarian carcinomas and have little or no evidence of skeletal disease (Andrew F. Stewart and Arthur E. Broadus, in *Endocrinology and Metabolism*, Felig et al. (eds.), 2d ed., McGraw-Hill, New York, 1987, pp. 1317–1453). The agent responsible for this paraneoplastic syndrome is not parathyroid hormone itself but is instead a novel peptide which is capable of interacting with parathyroid hormone receptors in some, but not all, target tissues.

The structure and sequence of the causative agent of HHM have heretofore eluded scientists. Experimental results (Stewart et al. [I], *N. Engl. J. Med.* 303:1377–83, 1980; Godsall et al., in *Recent Progress in Hormone Research*, Greep (ed.), 40, Academic Press, Orlando, Fla., 1986, pp. 705–50; Stewart et al. [II], "Identification of Adenylate Cyclase-Stimulating Activity and Cytochemical Glucose-6-Phosphate Dehydrogenase-Stimulating Activity in Extracts of Tumors from Patients with Humoral Hypercalcemia of Malignancy," *Proc. Natl. Acad. Sci. USA* 80:1454–58, 1983; Stewart et al. [III], "Frequency and Partial Characterization of Adenylate Cyclase-Stimulating Activity in Tumors Associated with Humoral Hypercalcemia of Malignancy," *J. Bone Miner. Res.* 1:267–76, 1986; Burtis et al., *Endocrinology* 118:1982–88, 1986; Insogna et al., "Biochemical and Histomorphometric Characterization of a Rat Model for Humoral Hypercalcemia of Malignancy," *Endocrinology* 114:888–96, 1984; Goltzman et al., *J. Clin. Endocrinol. Metab.* 53:899–904, 1981; Broadus et al., "Messenger Ribonucleic Acid from Tumors Associated with Humoral Hypercalcemia of Malignancy Directs the Synthesis of a Secretory Parathyroid Hormone-Like Peptide," *Endocrinology* 117:1661, 1985; Strewlet et al., *J. Clin. Invest.* 71:769, 1983; Rodan et al., *J. Clin. Invest.* 72:1511–15, 1983; and Rabbani et al., *Endocrinology* 118:1200–10, 1986) have suggested that the responsible mediator may be a tumor-derived 'parathyroid hormone (PTH)-like adenylate cyclase-stimulating protein which acts upon PTH receptors in the skeleton and the kidney but which differs from native PTH with respect to size, immunoreactivity and encoding mRNA.

Stewart et al. II and Stewart et al. III describe the partial purification of a human HHM tumor-derived PTH-like adenylate cyclase-stimulating protein by virtue of its ability to stimulate a canine renal cortical, PTH-sensitive, adenylate cyclase assay and to stimulate a fetal bone resorption bioassay.

The PTH-Like Peptide is an adenylate cyclase-stimulating protein which acts through parathyroid hormone receptors but which is unrelated genomically to PTH. It was observed in patients with HHM when evaluating nephrogenous cyclic AMP (NcAMP) excretion that:

1. Patients with MAHC can be subdivided into two groups depending upon whether their NcAMP values are elevated or suppressed.

2. Those patients with elevated NcAMP have predominantly squamous and renal carcinomas, tumors commonly inked to the HHM syndrome. These patients have few or no bone metastases.

3. The groups of patients with suppressed NcAMP excretion have predominantly breast carcinoma or hematologic malignancies, and display evidence of widespread skeletal invasion by tumor.

4. Eighty-two percent (41 out of 50) of the patients evaluated were in the elevated NcAMP group, suggesting that HHM may be far more common than previously appreciated.

5. Normocalcemic patients with cancer have normal NcAMP excretion.

6. When compared to a group of patients with primary hyperparathyroidism, both HHM groups of patients have markedly elevated values for fasting or fractional calcium excretion, reduced values for circulating 1,25-dihydroxyvitamin D ($1,25(OH)_2D$), and reduced or undetectable values for circulating and immunoreactive parathyroid hormone (PTH).

These results have been interpreted to indicate that the PTH-Like Peptide interacts with the same proximal tubular PTH receptor/adenylate cyclase complex as does PTH. Further, the PTH-Like Peptide is unlike PTH because: (1) the PTH-Like Peptide fails to stimulate the proximal tubular 1-hydroxylase responsible for $1.25(OH)_2D$ synthesis; (2) the PTH-Like Peptide may be unable to stimulate distal tubular calcium reabsorption; and (3) the PTH-Like Peptide fails to interact, unlike PTH, with a series of region-specific PTH antisera.

Bone histology was investigated in patients with HHM and with primary hyperparathyroidism. Like patients with primary hyperparathyroidism, osteoclastic bone resorption is accelerated in HHM. In fact, the degree of bone resorption is strikingly increased beyond that encountered in primary hyperparathyroidism. Unlike patients with primary hyperparathyroidism, however, osteoblastic activity is markedly reduced in patients with HHM, indicating that bone cell activity is uncoupled in HHM, and also indicating that the mechanism of action of the PTH-Like Peptide on a given target organ may be similar to, but different from, the effects of PTH on the same target organ.

The PTH-Like Peptide is a PTH receptor agonist. This statement is supported by observations that:

1. Patients with HHM display elevated nephrogenous cyclic AMP excretion.

2. Extracts of tumors and tumor-conditioned medium from both human and animal HHM-derived tumors stimulate adenylate cyclase activity in renal cortical membranes and clonal osteoblast-like cells; and 3. Adenylate cyclase-stimulating activity is competitively inhibitable with synthetic PTH analogs, which indicates that these extracts or conditioned medium stimulate adenylate cyclase via PTH receptors.

Partial purification of PTH-Like Peptide through HPLC and SDS-PAGE slices found the peptide to be sensitive to oxidation but insensitive to extreme reducing conditions. These findings are similar to those of PTH (which contains methionine residues but no disulfide bonds).

SUMMARY OF THE INVENTION

Briefly stated, the present invention provides a means to facilitate the diagnosis and treatment of HHM in cancer patients and to diagnose a malignancy if HHM is one of the symptoms of the disease. This invention is the complete sequence of human PTH-Like Peptide, comprising a 2.0 kilobase cDNA sequence which encodes a 141 amino acid peptide and a 36 amino acid leader segment. The second sequence of PTH-Like Peptide in FIGS. 1 and 8 comprises a 1.3 kilobase cDNA sequence which encodes a 166 amino acid peptide and a 36 amino acid leader segment.

The sequence of the larger cDNA contains a 531-base pair open reading frame flanked by 938- and 472-base 5' and 3' untranslated regions and a 60-base poly(A) tail. The open reading frame encodes a protein of 177 amino acids, consisting of a 36 amino acid leader sequence and a 141 amino acid mature peptide having a calculated molecular weight of 16,043 daltons. The 36 amino acid leader sequence has a positively charged N-terminus, a strongly hydrophobic central region, and the C-terminal dibasic residues Lys-Arg as an endoproteolytic cleavage site. The leader sequence is the same for both clones.

The cDNA sequence of FIG. 1 encodes the PTH-Like Peptide comprising the 141 amino acid mature peptide. This invention is the DNA sequence, a recombinant DNA molecule comprising a DNA sequence encoding a PTH-Like Peptide-type polypeptide, said sequence being selected from the group consisting of: the DNA insert consisting of he 2001-base sequence in FIG. 1, or shortened versions thereof; DNA sequences which hybridize to the foregoing DNA insert and which code for a PTH-Like Peptide-type polypeptide; and DNA sequences which are generated as a result of any of the foregoing DNA sequences and which code for a PTH-Like Peptide-type polypeptide. The invention further comprises a host cell transformed with the recombinant DNA molecule and a method of preparing a protein having substantially the same biological activity as a PTH-Like Peptide.

Knowledge of this sequence can enable the PTH-Like Peptide to be used as a tumor marker for cancer diagnosis and the differential diagnosis of hypercalcemia, and immunoconjugate targeting for receptor antagonist development to prevent the symptoms of HHM in susceptible cancer patients. Furthermore, knowledge of the sequence of human PTH-Like Peptide can enable the development of protein derivatives with antagonist activity.

DESCRIPTION OF THE DRAWINGS

FIG. 1 is the nucleotide sequence and the deduced amino acid sequence of cDNA from clone HHM-8. The numbering of the nucleotides and amino acids is shown as "+" or "−" relative to the sequence of the mature peptide; the region of relative homology to the PTH peptide is underlined in the amino acid sequence. The region corresponding to the oligonucleotide probe of Example 4 is overlined in the nucleotide sequence. Nucleotides 424–426 of this sequence constitute the stop codon.

FIG. 2 is a physical map of cDNA clone, λ HHM-8. The coding region is shaded. The initiating Met, the first amino acid of the mature peptide, and the end of the structural gene sequence of the peptide are indicated below the map. Restriction sites are shown above the map.

FIG. 3 shows the region of homology between the human PTH-Like Peptide and human PTH. Common nucleotides are indicated by an asterisk, and shared amino acids are underlined in the peptide sequence. The first amino acid in rat and bovine PTH is Ala, which is encoded by the OCT sequence.

FIG. 4 shows the complementary oligonucleotide prepared to amino acid residues 6–18 of the N-terminal sequence of a PTH-Like Peptide purified from a human breast carcinoma. The second line shows all possible mRNAs encoding this sequence. "N" represents A, C, G and T; "Pu" represents A and G; and "Py" represents T and C. The complementary 38-base oligonucleotide in line 3 contains four inosine residues ("I") and was constructed using optimum human codon choices. Line 4 shows the segment of the sequence of the isolated cDNA which is complementary to the probe. Nucleotides that differed from the probe are underlined.

FIG. 8 is the nucleotide sequence and the deduced amino acid sequence of cDNA from clone HHM-4. The beginning of the sequence to nucleotide 416. is shown in FIG. 1. Nucleotide 417 is the point of divergence and this different sequence resumes in FIG. 8. Nucleotides 499–501 of this sequence constitute the stop codon.

DETAILED DESCRIPTION OF THE INVENTION

Figure 5:
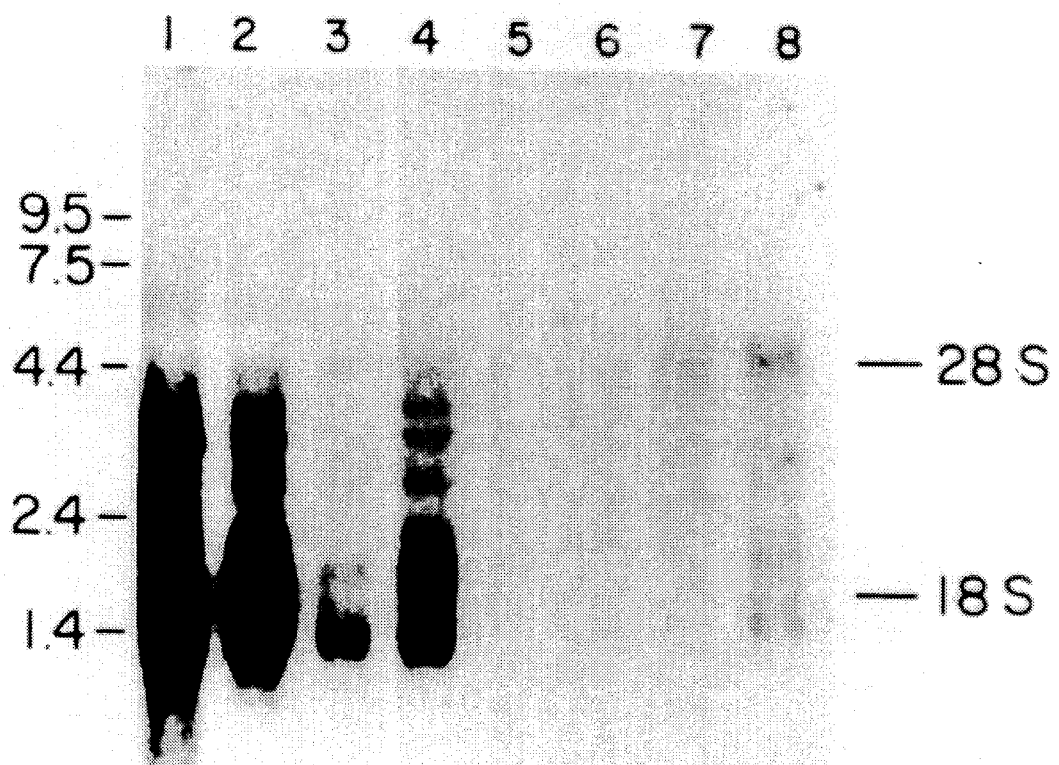
FIG. 5 is a Northern blot analysis of mRNA prepared from four carcinomas associated with HHM, three "negative" or non-HHM renal carcinomas and normal human keratinocytes. The mRNAs were prepared from: (lane 1) the breast carcinoma from which the disclosed peptide sequence was obtained, (lane 2) a human squamous carcinoma (YSC-B) which induces hypercalcemia in the athymic mouse and which is markedly enriched in PTH-Like Peptide activity based upon oocyte injection and bioassay (CBA 600 pgeq/ml when injected at 100 ng/oocyte), (lane 3) renal carcinomal line SKRC-52, (lane 4) renal carcinoma line SKRC-4, (lanes 5, 6 and 7) renal carcinoma lines SKRC-29, SKRC-42 and C, which do not secrete PTH-like activity and which also do not induce hypercalcemia when implanted in athymic mice, and (lane 8) normal human keratinocytes. The markers to the left correspond to the RNA ladder from Bethesda Research Laboratories. The locations of 28S and 18S rRNA are shown to the right. Weak cross-hybridization with 28S rRNA was noted in lanes 4, 7 and 8.

Prior to setting forth the invention, it may be helpful to an understanding thereof to set forth definitions of certain terms to be used hereinafter.

Polypeptide: A polymer of amino acids.

Reading frame: The arrangement of nucleotide codons which encode an uninterrupted stretch of amino acids. During translation of an mRNA, the proper reading frame must be maintained. For example, the sequence GCUGG-UUGUAAG may be translated into three reading frames, or phrases, depending on whether one starts with G, with C, or with U, and thus may yield three different peptide products. Translation of the template begins with AUG codon, continues with codons for specific amino acids, and terminates with one of the translation termination codons.

Coding sequence: DNA sequences which, in the appropriate reading frame, directly code for the amino acids of a protein.

Leader sequence: An amino acid sequence which occurs at the amino terminus of some proteins and is generally cleaved from the protein during translation. Leader peptides comprise sequences directing the protein into the secretion pathway of the cell. As used herein, the term "leader peptide" may also mean a portion of the naturally occurring leader peptide. The leader sequence in FIG. 1 begins with nucleotide -108 and extends to nucleotide -1.

Complementary DNA or cDNA: A DNA molecule or sequence which has been enzymatically synthesized from the sequences present in an mRNA template.

Transformation: The process of stably and heritably altering the genotype of a recipient cell microorganism by the introduction of purified DNA. This is typically detected by a change in the phenotype of the recipient organism.

Transcription: The process of producing mRNA template from a structural gene.

Expression: The process, starting with a structural gene, of producing its polypeptide, being a combination of transcription and translation. An expression vector is a plasmid-derived construction designed to enable the expression of a gene carried on the vector.

Plasmid: An extrachromosomal, double-stranded DNA sequence comprising an intact "replicon," such that the plasmid is replicated in a host cell. When the plasmid is placed within a unicellular organism, the characteristics of that organism may be changed, or transformed, as a result of the expression of the DNA sequences of the plasmid. For example, a plasmid carrying the gene for tetracycline resistance transforms a cell previously sensitive to tetracycline into one which is resistant to it.

Expression vector: Includes vectors which are capable of expressing DNA sequences contained therein, where such sequences are operably linked to other sequences capable of effecting their expression, such as promoter sequences. It is implied, although not always explicitly stated, that these expression vectors must be replicable in the host organism either as episomes or as an integral part of the chromosomal DNA. Clearly a lack of replicability would render the expression vectors effectively inoperable. A functional definition of an expression vector is any DNA sequence which is capable of effecting expression of a specified DNA code disposed therein. In general, expression vectors of utility in recombinant DNA techniques are often in the form of plasmids, which refer to circular, double-stranded DNA loops which, in their vector form, are not bound to the cellular chromosome. "Plasmid" and "vector" are often used interchangeably as the plasmid is the most commonly used form of vector. However, the invention is intended to include such other forms of expression vectors which serve equivalent functions and which become known in the art subsequently hereto.

Transformed host cells: Cells which have been transformed with recombinant DNA molecules using recombinant DNA techniques. As defined herein, PTH-Like Peptide is produced in the amounts achieved by virtue of this transformation, rather than in such lesser amounts, or, more commonly, in such less than detectable amounts as might be produced by the untransformed host.

PTH-Like Peptide biological activity is measured in terms of glucose-6-phosphate dehydrogenase (G6PD) activation in renal tubular cells and by stimulation of adenylate cyclase activity in renal and bone cell assay systems. The assay described in Goltzman et al., "Cytochemical Bioassay of Parathyroid Hormone: Characteristics of Assay and Analysis of Circulating Hormonal Forms," *J. Clin. Invest.* 65:1309, 1980, has been used to assay PTH-Like Peptide in the serum of patients with HHM (see Goltzman et al., "Malignancy-Associated Hypercalcemia: Evaluation with a Cytochemical Bioassay for Parathyroid Hormone," *J. Clin. Endocrinol. Metab.* 53:899–904, 1981).

Such an assay can be performed, for example, by preincubating kidney cortex segments, preferably obtained from Hartley strain albino guinea pigs weighing about 450–550 grams, for five hours at 37° C. in nonproliferative synthetic culture medium (Trowell's T medium, Grand Island Biological Co. (GIBCO), Grand Island, N.Y.), at pH 7.6 in an atmosphere of 95% $O_2$ and 95% $CO_2$. After incubation in fresh medium for eight minutes, each kidney cortex segment is additionally cultured with the sample, which can include one of the following: (1) PTH hormone standard (purified bovine PTH, MRC research standard), (2) cAMP or dibutyryl cAMP (Sigma Chemical Co., St. Louis, Mo.), (3) prostaglandin $E_1$ or $E_2$ (The Upjohn Co., Kalamazoo, Mich.), (4) dilutions of unfractionated plasma (1:100 to 1:1000), (5) pooled gel filtration eluates (1:20), or (6) tissue culture medium (1:100 and 1:1000). The segments are then chilled by immersion in n-hexane at −70° C. for 30–60 seconds and subsequently cut into 16 μm sections at −70° C. Unfixed sections are then reacted for G6PD activity employing a reaction medium containing 5 mM G6PD, 3 mM NADP, 0.67 mM phenaxine methosulfate, 5 mM neotetrazolium chloride, 10 mM KCN, and 12% polyvinyl alcohol in 0.05M glycyl glycine buffer, pH 8.0. The intensely colored formazan resulting from the reaction is then measured in the distal convoluted tubule cells of the kidney segments by scanning and integrating microdensitometry at 585 nm. For immunoabsorption studies, samples are incubated with antibovine PTH (anti-bPTH) guinea pig serum (AS 211/32) for one hour at 4° C. at a final dilution of 1:5000 before the bioassay.

PTH-Like Peptide biological activity is defined in PTH sensitive biological assays. On a weight or molar basis, this activity may be less than, equal to, or even greater than that of native PTH or its active synthetic fragments. The potency as defined by these assays is assay-specific, in that both the tumor-derived product and its synthetic amino-terminal fragment(s) are more potent in bone-derived than in kidney-derived biological assays, indicating that the PTH-Like Peptide preferentially interacts with certain PTH receptors such as those in bone (Stewart et al., *J. Bone Min. Res.* 2:37–43, 1987; Horiuchi et al., *Science* 238:1566–1568, 1987; Kemp et al., *Science* 238:1568–1570, 1987; Stewart et al., *J. Clin. Invest.* 81:596–600, 1988).

Human tumor-derived, PTH-like adenylate cyclase-stimulating protein was partially purified and partially characterized and found to have a molecular weight of 17,000 daltons and a specific activity of 410 μg eq of PTH (1–34)/ mg of protein (Burtis et al., "Identification of a Novel 17,000-Dalton Parathyroid Hormone-Like Adenylate Cyclase-Stimulating Protein from a Tumor Associated with Humoral Hypercalcemia of Malignancy," *J. Biol. Chem.* 262: 7151–56, 1987). The actual molecular weight of PTH-Like Peptide is calculated to be 16,043 daltons from clone 8 in FIG. 1.

The clinical profile of PTH-like adenylate cyclase-stimulating protein such as PTH-Like Peptide, includes hypercalcemia. Hypercalcemia occurs in the presence of a few or no bone metastases and is associated with increased nephrogenous cyclic AMP, reduced circulating 1,25-dihydroxy vitamin D concentrations, and normal or reduced circulating concentrations of immunoreactive PTH.

The human tumor-derived, PTH-like adenylate cyclase-stimulating protein or a similar protein is produced by a benign tumor (Stewart et al. IV, *Ann. Intern. Med.* 102:776–79, 1985) and by normal, nonmalignant, squamous cells in culture (Merendino et al., "A Parathyroid Hormone-Like Protein from Cultured Human Keratinocytes," *Science* 231:383–90, 1986).

As noted above, PTH-Like Peptide has been shown to the major secretory protein of tumors that cause HHM symptoms in cancer patients. The cDNA contains a 531-base pair opening reading frame flanked by 938- and 472-base 5' and 3' untranslated regions and a 60-base poly(A) tail. This sequence displays typical features of eucaryotic mRNA, including a purine residue at position -3 relative to the initiating ATG and the polyadenylation signal AATAAA 15 bp upstream from the poly(A) tail.

Figure 7:
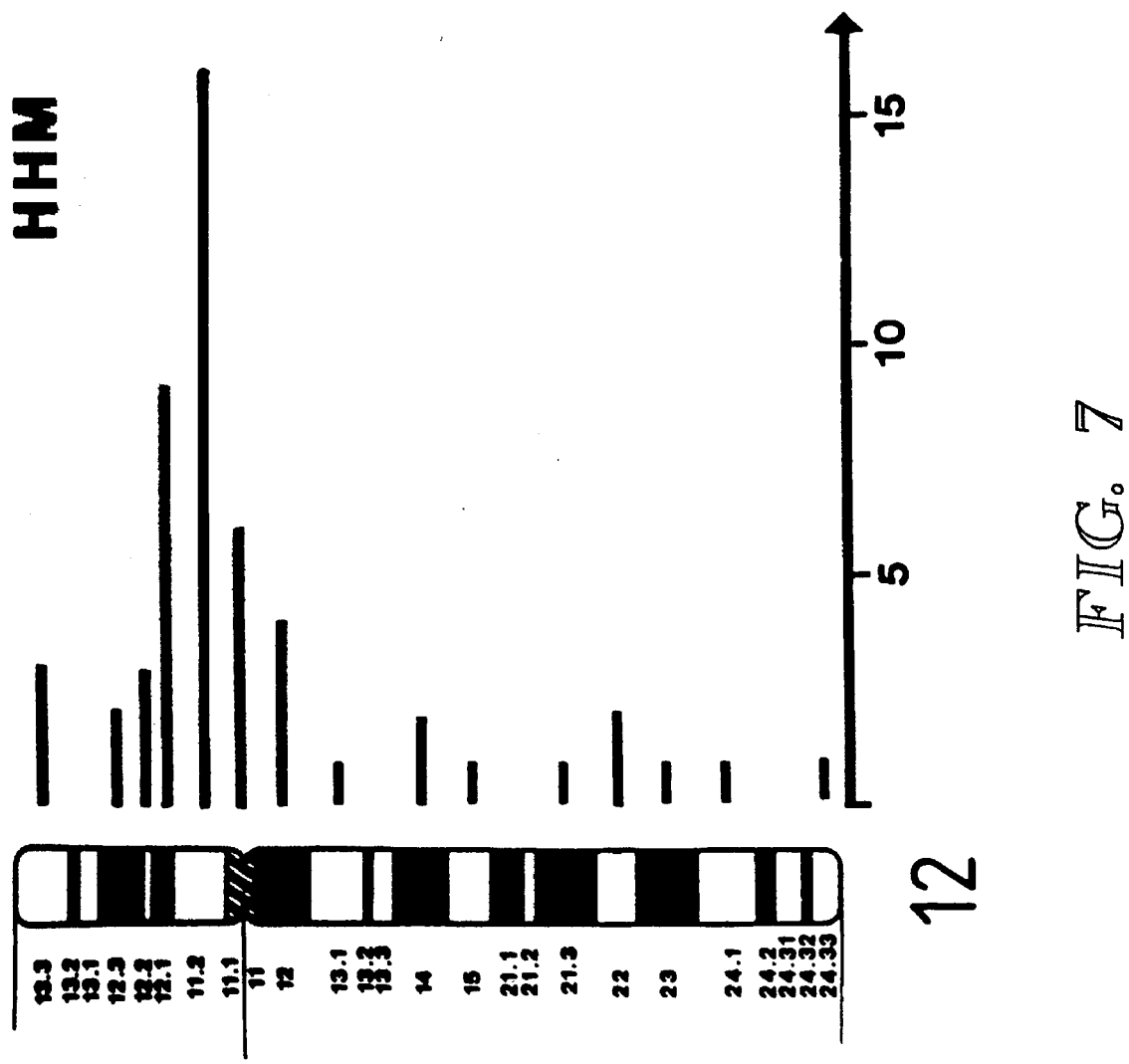
FIG. 7 shows the distribution of autoradiographic silver grains over human chromosome 12 after in situ hybridization with tritiated DNA insert. The scale at the bottom refers to the number of grains associated with specific chromosome bands and subbands. The specific sequence disclosed is localized at 12p11.2→p12.1.

The first 13 amine acids of the mature peptide display strong hemology to human PTH, but there is complete divergence thereafter, see FIG. 3. The sequence in the genomic form has been mapped to chromosome 12 (see FIG. 7). The genomic DNA from humans and rodents displays a simple pattern compatible with a single-copy gene.

The open reading frame encodes a protein of 177 amine acids, comprising a 36 amine acid leader sequence and a 141 amine acid mature peptide with a calculated molecular weight of 16,043 daltons. The leader sequence has the characteristic structure of a eucaryotic signal sequence, including a positively charged N-terminus and a strongly hydrophobic central region. The calculated molecular weight of the mature peptide is in good agreement with the size of the peptides (17,000 daltons) purified from the human breast carcinema and there is a close correspondence between the deduced and experimentally determined amine acid compositions. The deduced sequence contains 29 (21 percent) basic residues, in keeping with the pI of greater than 8.7 of the purified peptide. A number of these basic residues occur in short runs, particularly in the region from amine acids 88 through 108, in which 14 of 21 residues are basic. There are no Met or Cys residues and no potential sites of N-glycosylation. Comparisons with the EMBL and GertBank DNA libraries and NBRF protein data bank revealed no significant homologies with any known protein other than PTH in either nucleotide or amino acid sequence. The open reading frame of clone 4 (the 1.3 kilobase cDNA) encodes a protein of 202 amino acids, which is identical to that encoded by clone 8 (the 2.0 kilobase cDNA) through amino acid residue 139 of the mature peptide, at which point clone 4 diverges in sequence to encode a 166 amino acid mature peptide with 27 amino acids of unique C-terminal sequence. The calculated molecular weight of this 166 amino acid peptide is 18,887 daltons.

Recombinant PTH-Like Peptide can be made from the vectors and methods disclosed herein, over a wide range of host cells and a wide range of prokaryotic and eukaryotic organisms. Prokaryotes are preferred for cloning of DNA sequences in constructing the vectors useful in the invention. For example, *E. coli* K12 strain 294 (ATCC NO. 31,446) is particularly useful. Other useful microbial strains are, for example, *E. coli* strains such as *E. coli* X1776 (ATCC NO. 31,537) and *E. coli* B.

Prokaryotes may also be used for expression. Useful expression systems include the afore-mentioned *E. coli* strains, *E. coli* W3110 (F⁻, ⁻, prototrophic, ATCC NO. 27,325), bacilli such as *Bacillus subtilus,* and other enterobacteriaceae such as *Salmonella typhimurium* or *Serfaria marcesans,* and various pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is usually transformed using pBR 322, a plasmid derived from an *E. coli* species (Bolivar et al., *Gene* 2:95, 1977). The plasmid pBR 322 and other microbial plasmids contain genes for ampicillin and tetracycline resistance and these genes provide the means for identifying the transformed cells. The pBR 322 plasmid or other microbial plasmids must also contain, or be modified to contain, promoters which can be used by the microbial organism for expression of its own proteins. Those promoters often used in recombinant DNA construction include the -lactamase (penicillinase) and lactose promoter systems (Chang et al., *Nature*

275:615, 1978); Itakura et al., *Science* 198:1056, 1977; and Goeddel et al., *Nature* 281:544, 1979, and a tryptophan (trp) promoter system (Goeddel et al., *Nucleic Acid Res.* 8:4057, 1980 and European Patent Application EP-A-0036776). While these promoters are commonly used, other microbial promoters have been discovered and may be utilized. Details concerning their nucleotide sequences have been published, enabling a skilled worker to ligate them with plasmid vectors (Siebenlist et al., *Cell* 20:269, 1980).

In addition to prokaryotes, eukaryotic microorganisms, such as yeast cultures may also be used. *Saccharomyces cerevisiae,* or baker's yeast, is often the eukaryotic microorganism used and many strains are available for this purpose. For expression in Saccharomyces, the plasmid Rp7, for example (Stinchcomb et al., *Nature* 282:39, 1979; Kingsman et al., *Gene* 7:141, 1979; and Tschemper et al., *Gene* 10:157, 1980) is often used. The plasmid Rp7 contains the trp1 gene which confers a selection marker for a mutant strain of yeast lacking the ability to grow in tryptophan as, for example, in ATCC No. 44,076 or PEP4-1. (See Jones, *Genetics* 85:12, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255:2073, 1980), or other glycolytic enzymes (Hess et al., *J. Adv. Enzyme Req.* 2:149, 1968; and Holland et al., *Biochemistry* 17:4900, 1978), such as enolase, glyceraldehyde-3-phosphate dehydrogenase, hexokinase, pyruvate kinase, triosephosphate isomerase, phosphoglycose isomerase and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. (See Holland et al., *Biochemistry* 17:4900, 1978). In practice, any plasmid vector containing a yeast-compatible promoter, origin or replication and termination sequences is suitable.

In addition to microorganisms, cultures of cells derived from multicellular organisms may also be used as hosts. In principle, any such cell culture is workable, whether from vertebrate or invertebrate cellular sources. Interest, however, has been greater with cells from vertebrate sources. Examples of useful vertebrate host cell lines are VERO and HeLa cells, Chinese hamster ovary (CHO) cell lines, W138, BHK, COS-7, and MDCK cell lines. Expression vectors for such cells ordinarily include (if necessary) an origin of replication, a promoter located in front of or upstream to the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Simian Virus 40 (SV40) and cytomegalovirus. The early and late promoters of SV40 virus are particularly useful because both are obtained easily from the virus as a fragment which also contains the SV40 vital origin or replication (Fiers et al., *Nature* 273: 113, 1978). Smaller or larger SV40 fragments may also be used, provided there is included the approximately 250 bp sequence extending from the Hind III site toward the Bgl I site located in the vital origin of replication. Further, it is also possible, and often desirable, to utilize promoter or control sequences normally associated with the desired gene sequence, provided such control sequences are compatible with the host cell system.

An origin of replication may be provided either by construction of the vector to include an exogenous origin, such as may be derived from SV40 or other vital (e.g. Polyoma, Adeno, VSV, BPV source) or may be provided by the host cell chromosomal replication mechanism. If the vector is integrated into the host cell chromosome, the latter is often sufficient.

If cells without formidable cell membrane barriers are used as host cells, transfection is carried out by the calcium phosphate precipitation method as described by Graham and Van der Eb, *Virology* 52:546, 1978. However, other methods for introducing DNA into cells, such as by nuclear injection or by protoplast fusion may also be used. If prokaryotic cells or cells which contain substantial cell wall constructions are used, the preferred method of transfection is calcium treatment using calcium chloride as described in Cohen et al., *Proc. Natl. Acad. Sci. USA* 69:2110, 1972.

The construction of appropriate vectors containing the desired coding or control sequences employ standard ligation techniques. Isolated plasmids or DNA fragments are cleaved, tailored, and religated in the form desired to form the plasmids required. Cleavage is performed by treating with one or more restriction enzymes in buffer. Preferably, about 1 µg plasmid or DNA fragments is treated with about 1 unit of restriction enzyme in about 20 µl of buffer solution. The appropriate buffers and substrate amounts for each restriction enzyme is specified by the commercial source of the enzyme. Preferred incubation conditions are about 1 hour at about 37° C. After the incubation, the protein component is removed. This can be accomplished by extraction with phenol and chloroform. The nucleic acid component is recovered from the aqueous fraction by precipitation with ethanol.

For ligation, approximately equimolar amounts of the desired components, suitably end tailored to provide correct matching, are treated with about 10 units of T4 DNA ligase per 0.5 µg of DNA. When cleaved vectors are the components, it is preferable to pretreat with bacterial alkaline phosphatase to prevent religation of the cleaved vector.

The constructed plasmids are analyzed to confirm the correct sequences. The ligation mixtures are used to transform *E. coli* K12 strain 294 (ATCC 31,446). Successful transformants are selected by ampicillin or tetracycline resistance. Plasmids from the transformed cells are prepared and analyzed by restriction and/or sequenced by the method of Messing et al., *Nucleic Acid Res.* 9:309, 1981 or by the method of Maxam et al., *Methods in Enzymology* 65: 499, 1980.

The following examples are intended to illustrate but not to limit the invention.

EXAMPLE 1

Many clinical studies have indicated that HHM is common in cancer patients and that the responsible mediator in many instances has certain PTH-like actions but is not native PTH. We determined the sequence of the PTH-Like Peptide, both the nucleotide and amino acid sequences. We prepared a cDNA library from an mRNA which was both biologically and experimentally enriched. The cDNA library was size-selected for large inserts. The cDNA library was screened using a long (38-base), complementary, codon-preference oligonucleotide containing 4 inosine residues. The oligonucleotide was tested against the sequence of interest by the oocyte version of the hybrid-arrested translation assay. (Kawasaki, *Nucleic Acids Res.* 13:4991–5004, 1985). Most of the non-coding sequence for the PTH-Like Peptide gene was found at the 5' end of the cDNA.

EXAMPLE 2

Poly(A)+ RNA was prepared from four cell lines which secrete the HHM factor and was surveyed by oocyte injection and cytrochemical bioassay in an attempt to identify a biologically enriched source of the mRNA of interest. One line (SKRC-1) was considered enriched (cytochemical bioassay of 185 pgeg/ml) vis-a-vis the other three lines. Tumor from line SKRC-1 was grown in athymic mice, and mRNA from this line was further enriched by preparative polyacrylamide electrophoresis. The pool of mRNA in the 5 peak tubes from the experiment was 24-fold enriched.

EXAMPLE 3

A cDNA library was constructed in gt10 using 2 g of enriched mRNA from line SKRC-1. Because of the apparently large size of the mRNA, the cDNA was size-selected prior to insertion into the vector, achieving an average insert size of approximately 1500 bp.

EXAMPLE 4

An oligonucleotide probe was prepared using an Applied Biosystems synthesizer, purified on a 20% acrylamide/urea gel, and used to screen 100,000 plaques by filter hybridization. The oligonucleotide probe was a complementary 38-base probe prepared to amine acids 6–18 of the N-terminal sequence of the PTH-Like Peptide purified from a human breast carcinema. The peptide sequence of amine acids 6–18 and the mRNA library were derived from different tumor sources (see FIG. 4). Further, the breast carcinoma is only an occasional but not prototypical HHM-associated tumor. Therefore, the utility of the oligonucleotide probe to be used to screen the cDNA library was verified experimentally. The verification was accomplished in a hybridization-arrest experiment (Kawasaki, *Nucleic Acids Res.* 13:4991–5004, 1985) in which the preincubation of an excess of the oligonucleotide probe with the line SKRC-1 mRNA prior to injection into oocytes inhibited mRNA-dependent activity by greater than 99 percent.

Two strongly positive clones were identified and purified by sequential low-density plating. The two clones were termed "λHHM-4" and "λHHM-8." λHHM-4 contained an insert of 1.3 kb, whereas λHHM-8 contained a 2.0 kb insert.

EXAMPLE 5

The largest cDNA clone (λHHM-8) was analyzed in detail. The identity of this clone was determined in three ways. First, the N-terminal sequence of the peptide was identified in the predicted amino acid sequence of HHM-8. Second, the insert was subcloned into M13 and both strands used to hybrid-select mRNA from line SKRC-1 for oocyte injection and bioassay (Horwich et al., *Proc. Natl. Acad. Sci. USA* 80:4258–4262, 1983). The non-coding strand generated a strong (74 pgeq/ml) and the coding strand a negligible (4 pgeq/ml) signal. Third, the insert was subcloned into a pGEM vector in both orientations, and capped sense and anti-sense RNA were produced with T7 RNA polymerase. Oocyte injection with the sense RNA (5 ng/oocyte) produced and marked stimulation of the CBA (88 pgeq/ml), whereas negligible activity (2.4 pgeq/ml) was detected in media from anti-sense RNA-injected oocytes.

EXAMPLE 6

The λHHM-8 clone (clone-8) insert was used as a probe to examine the expression of transcripts encoding the PTH-Like Peptide in various tumors and tissues. Poly(A)+RNA prepared from three renal carcinomas unassociated with HHM failed to hybridize with the probe. Poly(A)+preparations from four tumors associated with HHM produced strong signals, and in each case, the hybridization pattern was complex (see FIG. 5). Line SKRC-1 contain two major hybridizing species of about 1.6 and 2.1 kb and three less abundant species of about 3.2, 3.8 and 4.2 kb (lane 4, FIG. 5). The five transcripts in this line were estimated to represent a total of 0.005 to 0.010 percent of the RNA load based on a comparison to known amounts of insert DNA. An identical hybridization pattern, more apparent on a longer exposure, was observed in RNA from a second renal carcinoma (lane 3, FIG. 5), and the breast carcinoma and squamous cell carcinoma each demonstrated 3 to 5 hybridizing transcripts. There was a good quantitative correlation between the intensities of the signals on the Northern blot and the biological activities determined previously for mRNA preparations. The keratinocyte RNA contained three hybridizing transcripts which were roughly equal in intensity and which appeared to co-migrate with the three transcripts of similar size in line SKRC-1 RNA. This finding is consistent with publications concerning the secretion of the PTH-Like Peptide by normal keratinocytes, and also indicated that the complex pattern of transcripts observed in the tumor-derived RNAs was not entirely a result of malignant transformation. These multiple hybridizing mRNA species appear to result from alternative RNA processing.

EXAMPLE 7

Figures 6A, 6B:
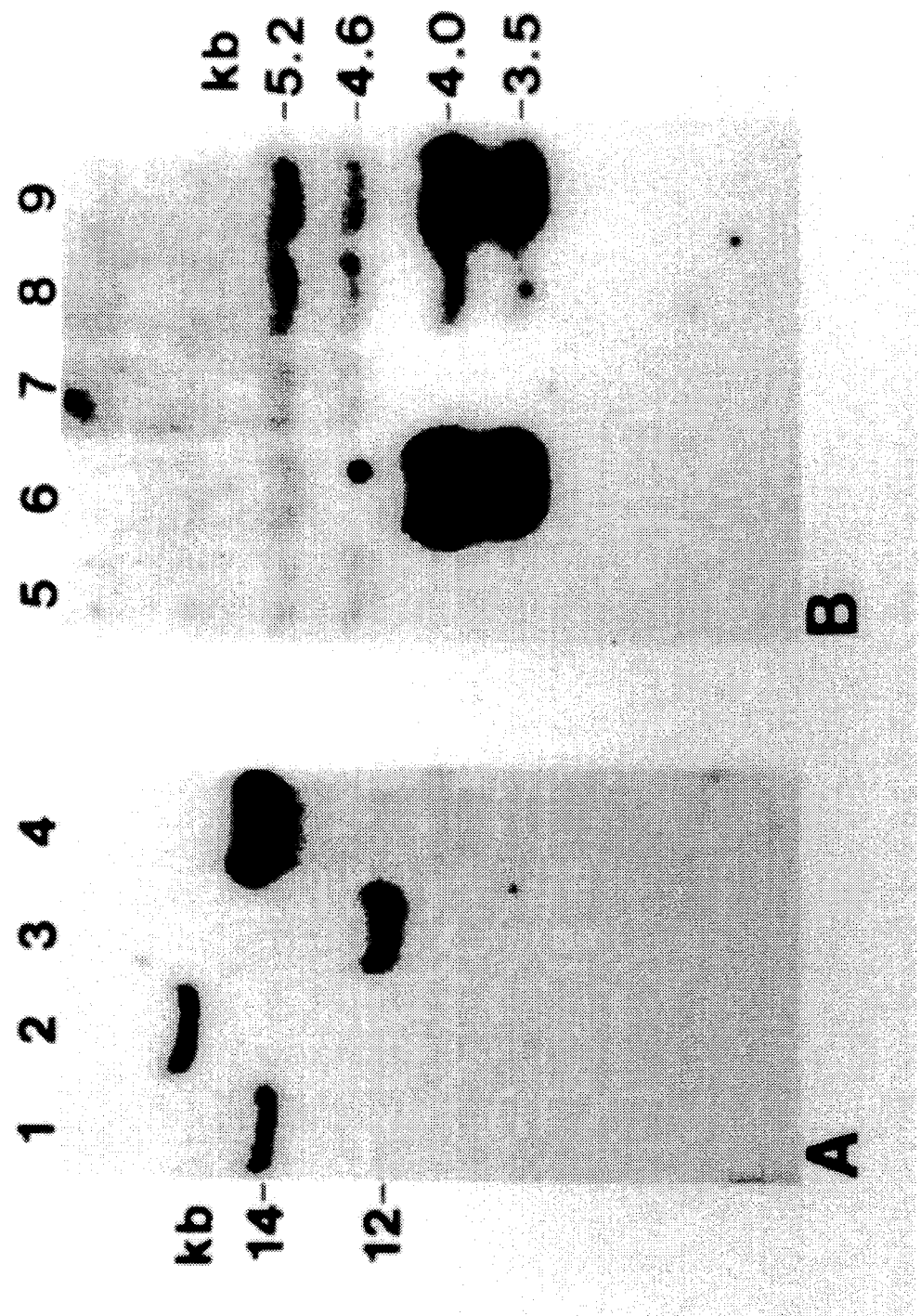
FIG. 6 is a Southern blot analysis of genomic HHM-related sequences. DNA from rat (lane 1), mouse (lane 2), Chinese hamster (lanes 3 and 5), human (lanes 4 and 6), or Chinese hamster×human hybrids (lanes 7–9) was digested with Eco RI (panel A) or Hind III (Panel B) and analyzed by Southern blot hybridization. The hybrid in lane 9 contains a human chromosome 12 with a terminal deletion of the long arm (12pter - q22) and is positive for the human 4.0- and 3.5-kb fragments. A 5.2-kb human Hind III fragment could not be distinguished from a similar sized Chinese hamster fragment. Additional weakly hybridizing fragments were seen in digests of human DNA (panel A, lane) but could not be scored in the hybrid cell lines.

Genomic Southern blotting analysis of mammalian DNAs with the λHHM-8 insert revealed a simple pattern compatible with a gene of low complexity (see FIG. 6). The insert detected a single strongly-hybridizing Eco RI fragment in DNA from human, rat, mouse and Chinese hamster cell lines, with the signal in the rodent DNAs being about one-third the intensity of that in the human DNA. Assignment of the gene for the PTH-Like Peptide to human chromosome 12 was made by analysis of Eco RI- or Hind III-digested DNA from 17 rodent×human hybrid cell lines. A single 14 kb Eco RI fragment or Hind III fragments of 4.0 and 3.5 kb were present in all hybrids containing human chromosome 12 and absent in all other hybrids. The sequences were present in a hybrid which carried a partial deletion of the distal long arm of chromosome 12. After in situ hybridization of tritiated insert to normal human metaphase chromosomes, 40 cells, of over 200 scored, had label on one or both chromosomes 12. The grain distribution pattern depicted in FIG. 7 indicates localization of the sequence on the proximal short-arm region p11.2 to p12.1.

EXAMPLE 8

The 1.3 kb clone, λHHM-4, was also sequenced and the sequence is shown in FIG. 8 beginning with point of divergence. The PTH-Like Peptide sequence was found to be identical to the λHHM-8 sequence through amino acid 139 or until amino acid 140, or the second-to-last amino acid at the C-terminal end. In the 2.0 kb clone (clone 8), this amino acid is Arg. In the 1.3 kb clone (clone 4), this amino acid was found to be Thr, based on the deduced amino acid sequence from the nucleotide sequence (see FIGS. 1 and 8). As shown in FIG. 8, the peptide encoded by λHHM-4 contains 27 amino acids of unique C-terminal sequence.

EXAMPLE 9

A diagnostic kit for the detection of the secretion of the PTH-Like Peptide by tumor or normal cells is prepared by isolating, synthesizing, or expressing the peptide or its analog in any of the expression systems described herein. The peptide or portions thereof is used to develop polyclonal antisera or clones of hybridoma cells secreting monoclonal antibodies specific for epitopes on the PTH-Like Peptide and isolated by standard hybridoma techniques. A monoclonal antibody or monoclonal antibody fragment, which is the proteolytic enzyme cleavage product of the whole monoclonal antibody (Fab, Fab' and F(ab')2 fragments) can be used to target PTH-Like Peptide from biological samples to determine qualitatively and quantitatively the amount of PTH-Like Peptide in a particular sample using standard immunoassay or solid phase techniques.

Alternatively, the DNA sequence of PTH-Like Peptide in FIG. 1 and/or FIG. 8 is used to develop an oligonucleotide probe. The oligonucleotide probe hybridizes to a segment of the DNA sequence of PTH-Like Peptide with at least 70 percent homology. The oligonucleotide probe is at least 12 nucleotide bases in length. The probe identifies enriched mRNA sequences in tumor cells that preferentially secrete PTH-Like Peptide and predisposing the host to HHM symptoms.

EXAMPLE 10

An immunoconjugate is prepared comprising a monoclonal antibody or monoclonal antibody fragment targeting protein as described in Example 9, and a therapeutic or diagnostic moiety linked directly to the targeting protein (covalentaly or non-covalently) or linked via a linking group to sterically separate the targeting protein from the therapeutic or diagnostic moiety. The immunoconjugate, if adminstered in vivo, targets circulating PTH-Like Peptide secreted in high concentrations with accompanying HHM symptoms. Further, if the humoral mediator of HHM remains within the tumor region, the immunoconjugate targets the tumor site for diagnostic imaging or for local site-specific therapeutic purposes. A therapeutic immunoconjugate contains a cytotoxic drug, toxin or radionuclide as its therapeutic moiety. A diagnostic immunoconjugate contains an imaging radionuclide within a chelating ligand linked to the targeting protein.

From the foregoing it will be appreciated that, although specific embodiments of the invention have been described herein for purposes of illustration, various modifications may be made without deviating from the spirit and scope of the invention.

We claim:

1. An isolated DNA molecule which encodes a any naturally occurring mammalian PTH-Like Peptide.

2. An isolated DNA molecule encoding a mammalian PTH-Like Peptide or a contiguous fragment thereof that has PTH receptor binding activity, said molecule being selected from the group consisting of:

(a) the DNA molecule of FIG. 1 from basepair -1046 to basepair 895 or portions thereof;

(b) said DNA molecule of FIG. 1 from basepair -1046 to basepair 416, wherein the nucleotides from the DNA molecule of FIG. 8 continue the sequence from basepair 417 to basepair 977, or portions thereof, (c) the DNA molecules which are degenerate as a result of the genetic code to the DNA molecules of subparagraphs (a) or (b) and which code for said PTH-Like Peptide or said contiguous fragment thereof that has PTH receptor binding activity.

3. The DNA molecule according to claim 2 wherein said molecule is obtained from human chromosome 12.

4. The DNA according to claim 2 wherein said DNA molecule is selected from the group consisting of the DNA molecules shown in FIG. 1 from nucleotide -1046 to nucleotide 895, nucleotide -108 to nucleotide 895, nucleotide 1 to nucleotide 895, nucleotide -108 to nucleotide 426, nucleotide -1046 to nucleotide 426, and nucleotide 1 to nucleotide 426.

5. The DNA molecule according to claim 2 wherein said DNA molecule which is shown to begin in FIG. 1 to nucleotide 416 and continue as shown in FIG. 8 resuming with nucleotide 417 is selected from the group consisting of molecules from nucleotide -1046 in FIG. 1 to nucleotide 977 in FIG. 8, nucleotide -108 in FIG. 1 to nucleotide 977 in FIG. 8, nucleotide 1 in FIG. 1 to nucleotide 977 in FIG. 8, nucleotide -1046 in FIG. 1 to nucleotide 501 in FIG. 8, nucleotide -108 in FIG. 1 to nucleotide 501 in FIG. 8, and nucleotide 1 in FIG. 1 to nucleotide 501 in FIG. 8.

6. A recombinant DNA molecule comprising a promoter operatively linked to an isolated DNA molecule which encodes a mammalian PTH-Like Peptide.

7. A recombinant DNA molecule comprising a promoter operatively linked to an isolated DNA molecule which encodes:

a mammalian PTH-Like Peptide or a contiguous fragment thereof that has PTH receptor binding activity, said molecule being selected from the group consisting of:

(a) the DNA molecule of FIG. 1 from basepair -1046 to basepair 895 or portions thereof;

(b) said DNA molecule of FIG. 1 from basepair -1046 to basepair 416, wherein the nucleotides from the DNA molecule of FIG. 8 continue the sequence from basepair 417 to basepair 977, or portions thereof;

(c) the DNA molecules which are degenerate as a result of the genetic code to the DNA molecules of subparagraphs (a) or (b) and which code for said PTH-Like Peptide or said contiguous fragment thereof that has PTH receptor binding activity.

8. The recombinant DNA molecule according to claim 7 wherein the DNA molecule is selected from the group consisting of the DNA molecules shown in FIG. 1 from nucleotide -1046 to nucleotide 895, nucleotide -108 to nucleotide 895, nucleotide 1 to nucleotide 895, nucleotide -108 to nucleotide 426, nucleotide -1046 to nucleotide 426, and nucleotide 1 to nucleotide 426.

9. The recombinant DNA molecule according to claim 7 wherein said DNA molecule is shown to begin in FIG. 1 to nucleotide 416 and continue as shown in FIG. 8 resuming with nucleotide 417 and is selected from the group consisting of molecules from nucleotide -1046 in FIG. 1 to nucleotide 977 in FIG. 8, nucleotide -108 in FIG. 1 to nucleotide 977 in FIG. 8, nucleotide 1 in FIG. 1 to nucleotide 977 in FIG. 8, nucleotide -1046 in FIG. 1 to nucleotide 501 in FIG. 8, nucleotide -108 in FIG. 1 to nucleotide 501 in FIG. 8, and nucleotide 1 in FIG. 1 to nucleotide 501 in FIG. 8.

10. The recombinant DNA molecule according to claim 7 wherein said promoter is selected from the group consisting of a lac system, a β-lac system, a trp system, major operator and promoter regions of phage λ, and the control region of fd coat protein promoters.

11. A host call transformed with a recombinant DNA molecule comprising a promoter operatively linked to an isolated DNA molecule which encodes a mammalian PTH-Like Peptide.

12. A host cell transformed with a recombinant DNA molecule comprising a promoter operatively linked to an isolated DNA molecule which encodes:

a mammalian PTH-like Peptide or a contiguous fragment thereof that has PTH receptor binding activity, said molecule being selected from the group consisting of:
  (a) the DNA molecule of FIG. 1 from basepair -1046 to basepair 895 or portions thereof;
  (b) said DNA molecule of FIG. 1 from basepair -1046 to basepair 416, wherein the nucleotides from the DNA molecule of FIG. 8 continue the sequence from basepair 417 to basepair 977, or portions thereof;
  (c) the DNA molecules which are degenerate as a result of the genetic code to the DNA molecules of subparagraphs (a) or (b) and which code for said PTH-Like Peptide or said contiguous fragment thereof that has PTH receptor binding activity.

13. The host cell transformed with a recombinant DNA molecule according to claim 12 wherein the DNA molecule is selected from the group consisting of the DNA molecules shown in FIG. 1 from nucleotide -1046 to nucleotide 895, nucleotide -108 to nucleotide 895, nucleotide 1 to nucleotide 895, nucleotide -108 to nucleotide 426, nucleotide -1046 to nucleotide 426, and nucleotide 1 to nucleotide 426.

14. The host cell transformed with a recombinant DNA molecule according to claim 12 wherein said DNA molecule is shown to begin in FIG. 1 to nucleotide 416 and continue as shown in FIG. 8 resuming with nucleotide 417 and is selected from the group consisting of molecules from nucleotide -1046 in FIG. 1 to nucleotide 977 in FIG. 8, nucleotide -108 in FIG. 1 to nucleotide 977 in FIG. 8, nucleotide 1 in FIG. 1 to nucleotide 977 in FIG. 8, nucleotide -1046 in FIG. 1 to nucleotide 501 in FIG. 8, nucleotide -108 in FIG. 1 to nucleotide 501 in FIG. 8, and nucleotide 1 in FIG. 1 to nucleotide 501 in FIG. 8.

15. The host cell transformed with a recombinant DNA molecule according to claim 12 wherein said promoter is selected from the group consisting of a lac system, a β-lac system, a trp system, major operator and promoter regions of phage λ, and the control region of fd coat protein promoters.

16. The transformed host cell according to claim 12 wherein said host cell is selected from the group consisting of prokaryotic and eukaryotic cells.

17. The transformed host cell according to claim 16, wherein said host cell is selected from the group consisting of strains of *E. coli,* Pseudomonas, *Salmonella typhimurium, Bacillus subtilis,* and *Bacillus stearothermophilus.*

18. A method of preparing a mammalian PTH-Like Peptide, comprising:

introducing into a host cell a recombinant DNA molecule capable of directing the expression and secretion of a mammalian PTH-Like Peptide, said recombinant DNA molecule containing a transcriptional promoter operatively linked to a DNA molecule encoding said PTH-Like Peptide, and a signal sequence capable of directing the secretion of the protein from the host cell;

growing said host cell in an appropriate medium; and isolating the protein product of said DNA molecule from said host cell.

19. The method of claim 18 wherein the host cell is a eukaryotic cell or a prokaryotic cell.

20. The method of claim 19 wherein the eukaryotic cell is a yeast cell.

21. The method of claim 19 wherein the prokaryotic cell is of bacterial origin.

22. The method of claim 21 wherein said host cell of bacterial origin is selected from the group consisting of strains of *E. coli,* Pseudomonas, *Salmonella typhimurium, Bacillus subtills,* and *Bacillus stearothermophilus.*

\* \* \* \* \*

UNITED STATES PATENT AND TRADEMARK OFFICE
CERTIFICATE OF CORRECTION

PATENT NO. : 5,605,815
DATED : 2/25/97
INVENTOR(S) : Arthur Broadus, Andrew Stewart, Marguerite Mangin It is certified that error appears in the above-identified patent and that said Letters Patent is hereby corrected as shown below:

Column 1, line 11, insert the following:

The invention identified above is a subject invention under 35 U.S.C. 200, et seq., and the Standard Patent Rights Clause at 37 C.F.R. 401.14 or F.A.R. 52.227-11, which are included among the terms of the grant/contract award from the Public Health Service/National Institutes of Health.

Signed and Sealed this

First Day of June, 1999

*Attest:*

Q. TODD DICKINSON

*Attesting Officer*  *Acting Commissioner of Patents and Trademarks*